(12) United States Patent
Chaudhari et al.

(10) Patent No.: US 9,629,800 B2
(45) Date of Patent: Apr. 25, 2017

(54) GASTRORETENTIVE FORMULATIONS AND MANUFACTURING PROCESS THEREOF

(75) Inventors: Mahendra Chaudhari, Naupada Thane (IN); Omprakash D. Chandwani, Ulhasnagar (IN); Rajashree S. Yelegaonkar, Badlapur (IN)

(73) Assignee: ETHYPHARM (FR)

( * ) Notice: Subject to any disclaimer, the term of this patent is extended or adjusted under 35 U.S.C. 154(b) by 1314 days.

(21) Appl. No.: 11/996,023

(22) PCT Filed: Jul. 19, 2006

(86) PCT No.: PCT/IB2006/002636
§ 371 (c)(1),
(2), (4) Date: Jan. 17, 2008

(87) PCT Pub. No.: WO2007/010400
PCT Pub. Date: Jan. 25, 2007

(65) Prior Publication Data
US 2008/0220060 A1 Sep. 11, 2008

(30) Foreign Application Priority Data
Jul. 19, 2005 (EP) .................... 05291542

(51) Int. Cl.
*A61K 9/28* (2006.01)
*A61K 9/16* (2006.01)
*A61K 9/00* (2006.01)
*A61K 9/20* (2006.01)

(52) U.S. Cl.
CPC .......... *A61K 9/0065* (2013.01); *A61K 9/1652* (2013.01); *A61K 9/205* (2013.01); *A61K 9/2054* (2013.01); *A61K 9/2826* (2013.01)

(58) Field of Classification Search
CPC .. A61K 9/0065; A61K 9/1652; A61K 9/2826; A61K 9/2054; A61K 9/205
See application file for complete search history.

(56) References Cited

U.S. PATENT DOCUMENTS

| | | | |
|---|---|---|---|
| 4,996,222 A * | 2/1991 | Carlin et al. | 514/400 |
| 6,261,601 B1 * | 7/2001 | Talwar et al. | 424/469 |
| 6,548,083 B1 | 4/2003 | Wong et al. | |
| 6,635,280 B2 | 10/2003 | Shell et al. | |
| 6,660,300 B1 | 12/2003 | Timmins et al. | |
| 6,797,283 B1 | 9/2004 | Edgren et al. | |
| 2003/0017189 A1 | 1/2003 | Wong et al. | |
| 2003/0232081 A1 * | 12/2003 | Doshi et al. | 424/472 |
| 2005/0058705 A1 * | 3/2005 | Remon et al. | 424/464 |

FOREIGN PATENT DOCUMENTS

| | | |
|---|---|---|
| EP | 0425154 A1 | 5/1991 |
| WO | 0164183 A1 | 9/2001 |
| WO | 03097018 A1 | 11/2003 |
| WO | WO2005060942 * 7/2005 | ............ A61K 9/22 |

OTHER PUBLICATIONS

Tuleu et al Drug Dev. And Industrial Pharm. p. 423, 1998.*
Schwartz et al Drug Dev & Ind. Pharm p. 1837 1985.*
International Search Report for PCT/IB2006/002636.

* cited by examiner

*Primary Examiner* — Suzanne Ziska
*Assistant Examiner* — Thurman Wheeler
(74) *Attorney, Agent, or Firm* — Sarika Singh; McNeely, Hare & War LLP.

(57) ABSTRACT

The present invention concerns gastroretentive formulation comprising an active substance granulated with a mixture of a weak gelling agent, a strong gelling agent, and a gas generating agent and process for manufacturing said formulation.

19 Claims, No Drawings

GASTRORETENTIVE FORMULATIONS AND MANUFACTURING PROCESS THEREOF

BACKGROUND OF THE INVENTION

The invention relates to gastroretentive formulations, in particular tablets, and to the process for manufacturing said formulations.

An important factor affecting the absorption of orally administered drug through gastro-intestinal tract is transit time in gastrointestinal tract.

Some active substances, for example metformin and ciprofloxacin, are known as being absorbed only from the stomach to the jejunum, i.e in the upper part of the gastrointestinal tract.

Hence, to achieve maximum efficiency with a minimum of active substance, it would be beneficial that the formulation be retained during a prolonged time in the stomach and allows therein a sustained release of the active substance.

Some attempts have already been done to achieve formulations with such a sustained release in the stomach, either thanks to the use of multilayer tablets such as in U.S. Pat. No. 6,797,283 (Edgren et al.), US patent application 20030232081, or thanks to tablets which are sufficiently small to be ingested and which swell after ingestion such as in U.S. Pat. No. 6,635,280 (Shell et al.) and U.S. Pat. No. 6,660,300 (Timmins et al.), and which further include disintegrating agent and effervescent agent, such as in U.S. Pat. No. 6,261,601 (Talwar et al.).

However, these formulations are not completely satisfactory and it still exists a need for formulations which are able to be retained in the higher part of the gastrointestinal tract and to release the active substance during several hours in the stomach.

SUMMARY OF THE INVENTION

Unexpectedly and surprisingly, the inventors have found that those objectives are fulfilled with a gastroretentive formulation comprising an active substance granulated with a mixture of a weak gelling agent, a strong gelling agent, and a gas generating agent.

In the present invention, a "weak gelling agent" is a compound presenting a viscosity of less than 175 centipoise when it is in a form of a 2.6% W/V aqueous dispersion at 25° C.

A "strong gelling agent" is a compound presenting a viscosity of at least 600 centipoise when it is in the form of a 1% W/V aqueous solution at 25° C.

Without being linked by any theory, it is thought that the weak gelling agent helps the matrix to swell faster due to its fast wetting property and the effervescent agent, which liberate gas on reaction with the gastric medium, helps to keep the tablet floating in the stomach. Use of a strong gelling agent provides rigidity to the swollen tablet matrix and helps to entrap the liberated gas in the tablet matrix.

In other words, as the acidic environment of the stomach enters in the core of the gelled matrix, it reacts with the gas liberating agent to liberate gas. The liberated gas gets entrapped in the gel matrix and releases slowly on the surface of the gelled matrix as the drug is diffused or delivered from the gelled matrix. The released gas gets adsorbed on the surface of the gelled matrix forming a bubbled layer on the surface and helps to control the dissolution or erosion of the gelled matrix in turn helping to control the release of the drug from the matrix. The composition remains in the stomach for long time releasing almost entire drug in the stomach for absorption.

DETAILED DESCRIPTION OF PREFERRED EMBODIMENTS

According to the present invention, the gastroretentive formulation is a monolithic pharmaceutical composition with sustained release effect, which is retained in the stomach from where the drug has maximum absorption for better therapeutic effect thereby acting as site specific drug delivery system.

The formulation is suitable for both highly soluble and/or partially soluble or poorly soluble drugs.

Due to this specific delivery system, the formulation according to the invention, is particularly useful for antibacterial substances of the fluoroquinolone class such as ciprofloxacin, ofloxacin, pefloxacin, grepafloxacin, enoxacin, amifloxacin, fleroxacin, temafloxacin, lomefloxacin, norfloxacin, sparfloxacin, levofloxacin, gatifloxacin and moxifloxacin, amoxicillin and Cephalexin derivatives in the form of base or salt thereof and also for antidiabetic substances such as metformin hydrochloride, Gliclazide, antihypertensive drugs such as diltiazem hydrochloride, metoprolol tartarate or succinate.

The amount of active substance ranges from 10 to 90%, preferably from 20 to 80% and even more preferably from 50 to 75% by weight of the total weight of the formulation.

The weak gelling agent is selected from the group comprising a co-processed material of microcrystalline cellulose and sodium carboxy methylcellulose, preferably the one sold under the trademark AVICEL® CL611, AVICEL® RC 581 and AVICEL® RC 591.

The strong gelling agent is selected from the group consisting of methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, xanthan gum, guar gum, carrageenan gum, locust bean gum, sodium alginate, agar-agar, gelatin, modified starches, co-polymers of carboxyvinyl polymers, co-polymer of acrylates, co-polymers of oxyethylene and oxypropylene and mixtures thereof.

The total amount of both weak and strong gelling agents ranges from 2 to 40%, preferably from 3 to 30% and even more preferably from 5 to 25% by weight of the total weight of the formulation.

The ratio of the weak gelling agent to the strong gelling agent ranges between 1:1 to 1:10, preferably from 1:2 to 1:8 and even more preferably between 1:3 to 1:5. The ratio of the substance active to both weak and strong gelling agents ranges from 1:99 to 99:1, preferably from 1:1 to 20:1, and even more preferably from 2:1 to 15:1

The gas generating agent is a compound which generates gas when it is in contact with an acidic medium, such as gastric fluid. Said gas generating agent is selected from the group consisting in water soluble carbonates, sulfites and bicarbonates, such as sodium carbonate, sodium bicarbonate, sodium metabisulfite, calcium carbonate, and mixtures thereof.

The amount of gas generating agent ranges from 5 to 30%, preferably from 10 to 25% and even more preferably from 12 to 22% by weight of the total weight of the formulation.

The gas generating agent may be present in the formulation according to the invention inside the granules of active substance or as an excipient of the formulation or both.

Thus, according to a first embodiment, at least a part of the gas generating agent is present in the granules of the active substance, i.e. at least a part of the gas generating agent is granulated together with the active substance and the mixture of weak and strong gelling agents, optionally with the other granulating agents; the remaining part of the gas generating agent being present with excipients of the formulation, i.e. not granulated with the active substance.

According to a second embodiment, the whole amount of the gas generating agent is present with the excipients of the formulation, i.e. is not granulated with the active substance and the mixture of weak and strong gelling agents, optionally with the other granulating agents.

The gastroretentive formulation according to the invention comprises an active substance granulated with a mixture of:
(A) a weak gelling agent selected from the group comprising co-processed material of microcrystalline cellulose and sodium carboxy methylcellulose, and
(B) at least one strong gelling agents selected from the group consisting of methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, xanthan gum, guar gum, carrageenan gum, locust bean gum, sodium alginate, agar-agar, gelatin, modified starches, co-polymers of carboxyvinyl polymers, co-polymer of acrylates, co-polymers of oxyethylene and oxypropylene and mixtures thereof, preferably it is xanthan gum,
(C) optionally a binder selected from the group consisting in low viscosity HPMC, PVP, polymethacrylic acid copolymer (Eudragit E 100) and mixtures thereof,
the formulation also comprises a gas generating agent.

According to a third embodiment of the invention, the active substance may also be granulated with at least one additive (D) selected from the group comprising diluent or anti-static agent such as colloidal silicon dioxide, or mixture thereof.

The amount of binder (C) ranges from 0 to 10%, preferably from 0.5 to 5%, and even more preferably from 1 to 3% by weight of the total weight of the formulation.

The granules used in the formulation of the present invention are prepared by wet granulation using a an alcoholic or hydro-alcoholic solution of said binder (C). Preferably, the alcohol used for granulation is ethyl alcohol or isopropyl alcohol.

The formulation according to the invention can further comprises excipients selected from the group consisting of diluents, lubricating agents, wetting agents, sweeteners, flavours, colorants and mixtures thereof.

Commonly used diluent may be lactose, dibasic calcium phosphate, microcrystalline cellulose and mixtures thereof.

Lubricating agents are conventionally used ones, such as stearates, in particular magnesium stearate, glyceryl behanate, colloidal silicon dioxide, and mixtures thereof.

Wetting agents may be polysorbates, sodium lauryl sulphates and mixtures thereof.

Preferably, the formulation according to the invention is a tablet.

The tablets may be film coated with suitable polymeric materials that are commonly used in the art of film coating. Film coating improves the appearance of the formulation, masks the unpleasant taste and/or improves the stability of the formulation by providing a protection from moisture and does not have any influence on the release rate of the drug from the composition.

The invention further relates to the process for manufacturing the formulation according to the invention.

According to a first embodiment, the process comprises the following steps:
(1) an active substance is dry mixed with a mixture of (A) a weak gelling agent and (B) a strong gelling agent and optionally at least one additive (D) selected from the group comprising diluent or anti-static agent or mixture thereof;
(2) optionally the obtained dry mix is granulated with at least one binder (C) dissolved in alcohol or alcohol and water mixture,
(3) the gas generating agent is dry mixed with granules obtained from step (2) optionally with excipients selected from the group comprising diluents, lubricating agents, wetting agents, sweetners, flavours, colorants and mixtures thereof,
(4) the mixture is then compressed into tablets;
(5) optionally the tablets are film coated.

According to a second embodiment, the process comprises the following steps:
(1) an active substance is dry mixed with a mixture of (A) a weak gelling agent and (B) a strong gelling agent and optionally at least one additive (D) selected from the group comprising diluent or anti-static agent or mixture thereof, and at least a part of a gas generating agent;
(2) optionally the obtained dry mix is granulated with at least one binder (C) dissolved in alcohol or alcohol and water mixture,
(3) the remaining part of the gas generating agent, if any, is dry mixed with granules obtained from step (2) optionally with excipients selected from the group comprising diluents, lubricating agents, wetting agents, sweetners, flavours, colorants and mixtures thereof,
(4) the mixture is then compressed into tablets;
(5) optionally the tablets are film coated.

The invention is further illustrated by the following examples.

EXAMPLES

Example 1

| Ingredient | Weight (mg/tab) | % w/w |
| --- | --- | --- |
| Metformin Hydrochloride | 510.0 | 57.47 |
| Avicel CL 611 | 30.00 | 3.45 |
| Xanthan gum | 145.00 | 16.67 |
| PVP K 30 | 17.00 | 1.95 |
| Sodium Bicarbonate | 176.00 | 20.23 |
| Magnesium Stearate | 2.0 | 0.23 |

Metformin Hydrochloride (2% Extra quantity taken), Avicel CL 611, xanthan gum were mixed together in a suitable mixer such as high shear mixer or planetary mixer.

The blend was granulated with a solution of PVP K 30 in isopropyl alcohol and water. The wet mass was dried in a drier till a moisture content between 3.5 to 5.5% was obtained.

The dried mass was calibrated through 20 mesh screen and mixed with sodium bicarbonate and magnesium stearate in a suitable blender.

The resultant blend was compressed into tablets using a rotary compression machine with 16 stations (Fette or Suvac type machine), at 880 mg tablet weight with tablet parameters as follows:
machine speed: 25 to 27 rpm.
Tablet shape—biconvex caplets
Size—length 19 mm and width 9 mm
Hardness—120 to 160 N The tablets were tested for dissolution in 0.1 N HCl using USP type II apparatus at 100 RPM. The dissolution results are as follows—

| Time in Hrs | Cumulative release percentage (expressed by weight) |
| --- | --- |
| 1 | 31.10 |
| 2 | 45.20 |
| 4 | 65.40 |
| 6 | 78.00 |
| 8 | 88.10 |
| 12 | 97.70 |

Example 2

| Ingredient | Weight (mg/tab) | % w/w |
| --- | --- | --- |
| Ciprofloxacin Base | 500.0 | 72.99 |
| Avicel CL 611 | 10.00 | 1.46 |
| Xanthan gum | 30.00 | 4.38 |
| Colloidal Silicon Dioxide | 25.00 | 3.65 |
| PVP K 30 | 10.00 | 1.46 |
| Sodium Bicarbonate | 85.00 | 12.41 |
| Magnesium Stearate | 25.0 | 3.65 |

Ciprofloxacin, Avicel CL 611, Xanthan gum, Colloidal Silicon Dioxide and sodium bicarbonate were mixed together in a suitable mixer such as high shear mixer or planetory mixer. The blend was granulated with a solution of PVP K 30 in isopropyl alcohol. The wet mass was dried in a drier till a moisture content between 1.5 to 3.0% was obtained. The dried mass was calibrated through 20 mesh screen and mixed with magnesium stearate in a suitable blender. The resultant blend was compressed in to tablets using a rotary tablet compression machine at 685 mg tablet weight with tablet parameters as follows:
Tablet shape—biconvex caplets
Size—length 16 mm and width 8 mm
Hardness—100 to 160 N
The tablets were coated with a coating solution having the following composition:

| lactose monohydrate: | 19.17% |
| --- | --- |
| Talc: | 2.87% |
| Titanium Dioxide: | 1.43% |
| Polysorbate 80: | 0.1% |
| water: | 76.39% |

The coating was carried out between 1.50 to 2% of the core weight of the tablet formulation.

The tablets were tested for dissolution in 0.1 N HCl using USP type II apparatus at 50 RPM. The dissolution results are as follows—

| Time in Hrs | Cumulative release percentage (expressed by weight) |
| --- | --- |
| 1 | 37.18 |
| 2 | 56.09 |
| 4 | 77.14 |
| 6 | 92.59 |
| 8 | 98.26 |

The invention claimed is:

1. A gastroretentive formulation comprising an active substance granulated with a mixture of:
    a weak gelling agent (A) which is a co-processed material of microcrystalline cellulose and sodium carboxy methylcellulose;
    a strong gelling agent (B), which is a compound having a viscosity of at least 600 centipoise when it is in the form of a 1% W/V aqueous solution at 25° C.; and
    a gas generating agent,
    wherein the gastroretentive formulation is monolithic, and wherein a ratio of the weak gelling agent (A) to the strong gelling agent (B) ranges from 1:1 to 1:10.

2. The gastroretentive formulation according to claim 1, wherein the strong gelling agent is selected from the group consisting of methyl cellulose, hydroxypropyl methyl cellulose, hydroxypropyl cellulose with the exclusion of low-substituted hydroxypropyl cellulose, hydroxyethyl cellulose, ethyl cellulose, sodium carboxymethyl cellulose, xanthan gum, guar gum, carrageenan gum, locust bean gum, sodium alginate, agaragar, gelatin, modified starches, co-polymers of carboxyvinyl polymers, co polymer of acrylates, co-polymers of oxyethylene and oxypropylene, and mixtures thereof.

3. The gastroretentive formulation according to claim 1, wherein the active substance is also granulated with a binder (C) and optionally with additives (D) selected from the group consisting of diluents, anti-static agents, and mixtures thereof.

4. The gastroretentive formulation according to claim 1, further comprising excipients selected from the group consisting of diluents, lubricating agents, wetting agents, sweeteners, flavours, colorants, and mixtures thereof.

5. The gastroretentive formulation according to claim 1, wherein the gas generating agent is selected from the group consisting of water soluble carbonates, sulfites, and bicarbonates, and mixtures thereof.

6. The gastroretentive formulation according to claim 3, wherein the binder is selected from the group consisting of low viscosity hydroxypropyl methylcellulose, polyvinyl pyrrolidone, polymethacrylic acid copolymer, and mixtures thereof.

7. The gastroretentive formulation according to claim 1, wherein the amount of active substance ranges from 10 to 90% by weight relative to the total weight of the formulation.

8. The gastroretentive formulation according to claim 1, wherein the total amount of both weak and strong gelling agents ranges from 2 to 40% by weight relative to the total weight of the formulation.

9. The gastroretentive formulation according to claim 1, wherein the ratio of the weak gelling agent to the strong gelling agent ranges from 1:2 to 1:8.

10. The gastroretentive formulation according to claim 1, wherein a ratio of the active substance to both weak and strong gelling agents ranges from 1:99 to 99:1.

11. The gastroretentive formulation according, to claim 1, wherein the active substance is selected from the group consisting of antibacterial substances of the fluoroquinolone class; amoxicillin, cephalexin, and derivatives of the foregoing in the form of base or salt thereof; antidiabetic substances; and anti-hypertensive drugs.

12. A process for manufacturing a formulation according to claim 1, comprising:
(1) dry mixing an active substance with a mixture of:
a weak gelling agent (A) which is a co-processed material of microcrystalline cellulose and sodium carboxy methylcellulose,
a strong gelling agent (B), which is a compound having a viscosity of at least 600 centipoise when it is in the form of a 1% W/V aqueous solution at 25° C. wherein a ratio of the weak gelling agent (A) to the strong gelling agent (B) ranges from 1:1 to 1:10,
and optionally at least one additive selected from the group consisting of a diluent,
an anti-static agent and mixtures thereof, and
at least a part of a gas generating agent;
(2) granulating the dry mix from the dry mixing step (1) with at least one binder dissolved in alcohol or an alcohol and water mixture to provide granules,
(3) dry mixing any remaining part of the gas generating agent with granules obtained from granulating step (2), optionally with excipients selected from the group consisting of diluents, lubricating agents, wetting agents, sweetners, flavours, colorants and mixtures thereof,
(4) compressing the dry mix into tablets;
(5) optionally film coating the tablets.

13. The gastroretentive formulation according to claim 9, wherein the ratio of the weak gelling agent to the strong gelling agent ranges from 1:3 to 1:5.

14. The gastroretentive formulation according to claim 10, wherein the ratio of the active substance to both weak and strong gelling agents ranges from 1:1 to 20:1.

15. The gastroretentive formulation according to claim 14, wherein the ratio of the active substance to both weak and strong gelling agents ranges from 2:1 to 15:1.

16. The gastroretentive formulation according to claim 7, wherein the amount of active substance ranges from 20 to 80% by weight relative to the total weight of the formulation.

17. The gastroretentive formulation according to claim 16, wherein the amount of active substance ranges from 50 to 75% by weight relative to the total weight of the formulation.

18. The gastroretentive formulation according to claim 8, wherein the total amount of both weak and strong gelling agents ranges from 3 to 30% by weight relative to the total weight of the formulation.

19. The gastroretentive formulation according to claim 18, wherein the total amount of both weak and strong gelling agents ranges from 5 to 25% by weight relative to the total weight of the formulation.

* * * * *